(12) United States Patent
Straka et al.

(10) Patent No.: US 9,675,450 B2
(45) Date of Patent: Jun. 13, 2017

(54) PERICARDIAL HEART VALVE REPLACEMENT AND METHODS OF CONSTRUCTING THE SAME

(75) Inventors: František Straka, Prague (CZ); Jaroslav Mašín, Cestlice (CZ); David Schorník, Prague (CZ); Jan Pirk, Prague (CZ)

(73) Assignees: Franisek Straka, Prague (CZ); David Schornik, Prague (CZ)

( * ) Notice: Subject to any disclaimer, the term of this patent is extended or adjusted under 35 U.S.C. 154(b) by 95 days.

(21) Appl. No.: 14/406,024

(22) PCT Filed: Aug. 17, 2012

(86) PCT No.: PCT/CZ2012/000083
§ 371 (c)(1),
(2), (4) Date: May 11, 2015

(87) PCT Pub. No.: WO2013/182171
PCT Pub. Date: Dec. 12, 2013

(65) Prior Publication Data
US 2015/0335422 A1    Nov. 26, 2015

(30) Foreign Application Priority Data

Jun. 5, 2012    (CZ) .............................. PV 2012-376

(51) Int. Cl.
*A61F 2/24*    (2006.01)
*A61L 27/36*   (2006.01)
*A61L 27/50*   (2006.01)

(52) U.S. Cl.
CPC .......... *A61F 2/2412* (2013.01); *A61F 2/2415* (2013.01); *A61F 2/2418* (2013.01);
(Continued)

(58) Field of Classification Search
CPC .. A61L 27/3604; A61F 2/2412; A61F 2/2418; A61F 2/30942
See application file for complete search history.

(56) References Cited

U.S. PATENT DOCUMENTS

| | | | |
|---|---|---|---|
| 5,554,184 A | * | 9/1996 | Machiraju ............. A61F 2/2412 606/167 |
| 2007/0150052 A1 | * | 6/2007 | Santilli .................. A61B 6/504 623/2.11 |
| 2008/0154355 A1 | * | 6/2008 | Benichou ............. A61F 2/2415 623/1.26 |

* cited by examiner

*Primary Examiner* — Brian Dukert
(74) *Attorney, Agent, or Firm* — Greenberg Traurig, LLP

(57) ABSTRACT

The pericardial heart valve replacement (1) is constructed from living tissue of autologous pericardium containing living pericardial interstitial cells (PICs) and a living extracellular matrix (ECM) in the following way: in the first step the size and shape of the patient's native pathological heart valve is determined using real-time three-dimensional transesophageal echocardiography (TEE) or computer tomography (CT angiography) or magnetic resonance imaging (MRI); in the next step a stented (2) or a stentless pericardial heart valve replacement (1) is constructed from a single sheet of living autologous pericardium obtained from the patient; the size and shape of the pericardial heart valve replacement (1) corresponds to the size and shape of the patient's native heart valve and aortic or pulmonary root. The subject matter of the invention also includes the development of a device (5) for the conditioning and modification of the living autologous pericardial heart valve replacement (1) consisting of a ipulsatile pump (6) driving the flow of culture medium in the device (5) to perfuse the cells in the pericardium, a reservoir (7) regulating the fluid capacitance and function of the pericardial heart valve replacement (1), a chamber (8) containing a holder (9) for the placement of the pericardial heart valve replacement (1) during dynamic (Continued)

conditioning, and a gas exchanger (10*a, b*) for perfusing $CO_2$ into the culture medium. The reservoir (7), the chamber (8) and the gas exchanger (10*a, b*) are placed in an incubator (11) with an inner atmosphere of air mixed with 5% $CO_2$ and a temperature of 36 to 37° C., the individual components of the device (5) being connected by tubing (12).

7 Claims, 15 Drawing Sheets

(52) U.S. Cl.
CPC ........ *A61F 2/2472* (2013.01); *A61L 27/3604* (2013.01); *A61L 27/3691* (2013.01); *A61L 27/507* (2013.01); *A61F 2240/001* (2013.01); *A61F 2240/002* (2013.01)

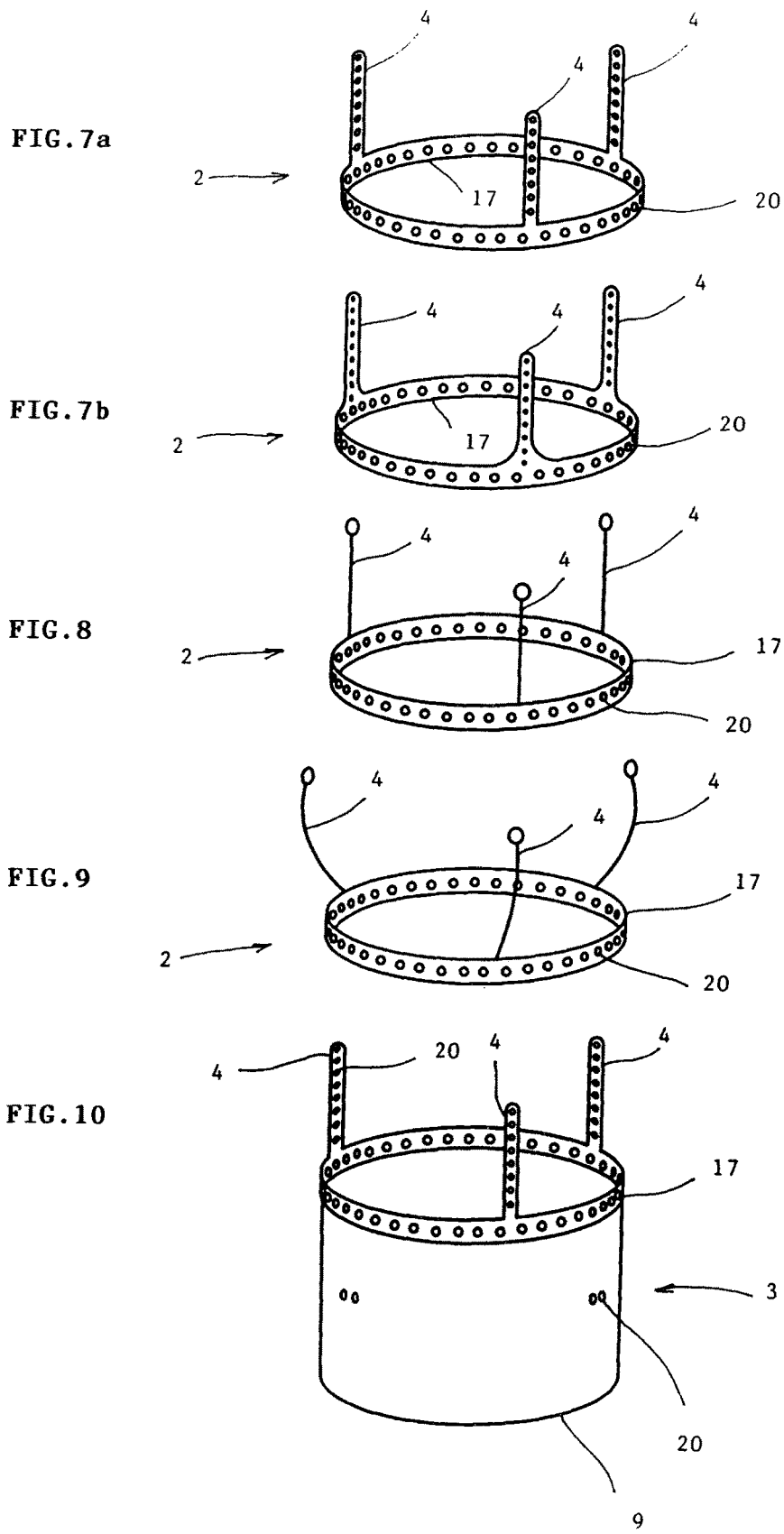

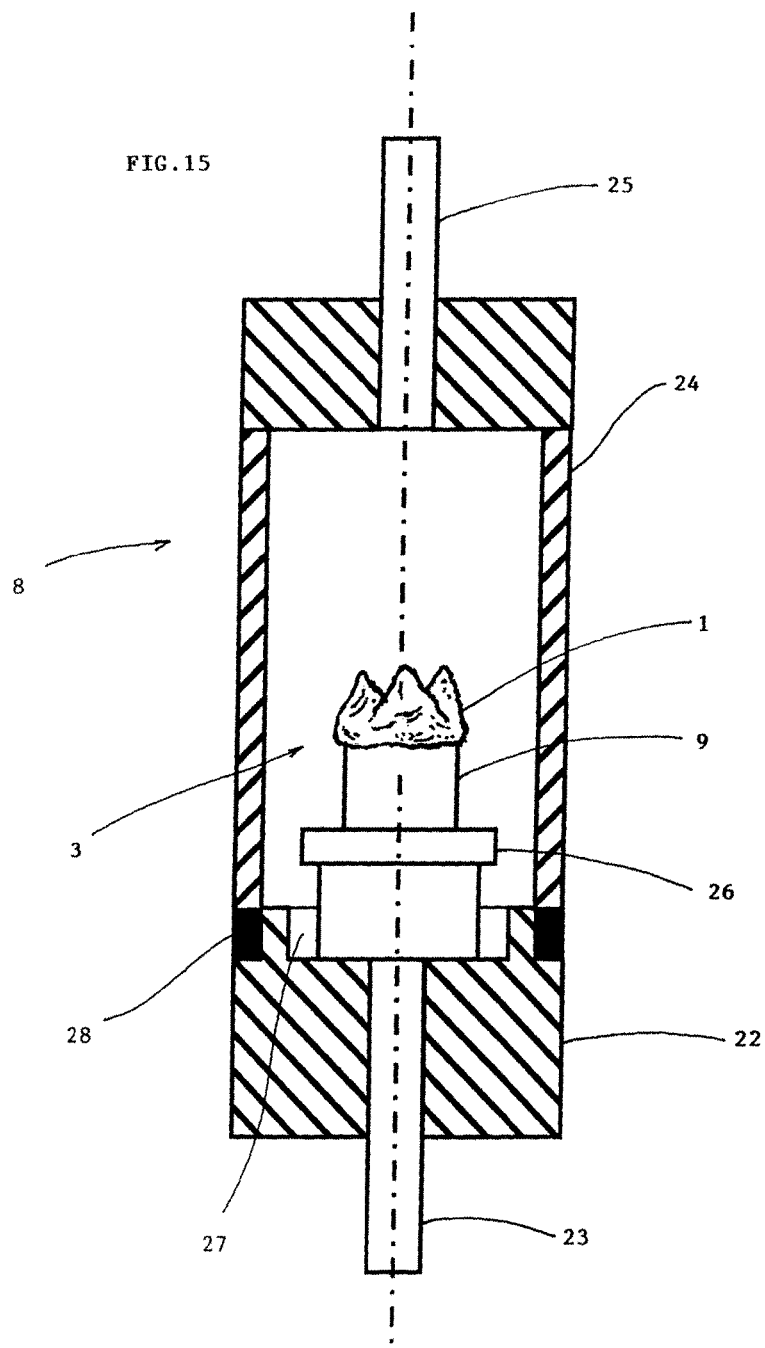

PERICARDIAL HEART VALVE REPLACEMENT AND METHODS OF CONSTRUCTING THE SAME

FIELD OF THE INVENTION

The present invention relates to a method of constructing a pericardial heart valve replacement, a pericardial heart valve replacement constructed according to this method, and a device for the in vitro conditioning and modification of tissue of autologous pericardium for use as a pericardial heart valve replacement.

BACKGROUND OF THE INVENTION

The implantation of heart valve replacements is an increasingly frequent medical procedure. One of the principal topics of cardiac surgery and cardiology is the construction of heart valve replacements for clinical use.

Presently, whole porcine valves are commonly used as heart valve replacements in humans or the cusps of heart valve replacements are constructed from bovine pericardium. The disadvantage of such heart valve replacements is that they are xenogeneic to the immune system of the human patient and thus immunogenic. The patient's immune system reacts to such heart valve replacements and induces the development of degenerative changes in the heart valve replacement necessitating re-operation for heart valve replacement failure. To avoid infection of xenogeneic heart valve replacements and the development of degenerative changes, xenogeneic heart valves are subjected to strict sterilization procedures using crosslinking agents and other chemical treatments, such as stabilization in glutaraldehyde. As a result, the tissue of such a heart valve replacement is nonliving when implanted into the heart of the patient. Such tissue is inert to the biological environment and does not allow the infiltration and colonization of host cells that are necessary for the remodeling and maintenance of normal living heart valve tissue. This leads to the accumulation of degenerative changes and eventual failure of the heart valve replacement. There is also the potential for glutaraldehyde and other chemical agents to leach from the xenogeneic crosslinked heart valve replacements with the risk of cytotoxic effects in the patient.

Artificially created extracellular matrices seeded with living autologous cells represent another alternative method of constructing a heart valve replacement using tissue engineering. For example, U.S. Pat. No. 5,899,937 describes the decellularization and subsequent colonization of the extracellular matrix (ECM) of a porcine aortic heart valve using autologous cells harvested from the patient's skin. The disadvantage of this approach is that a nonliving xenogeneic matrix is used which is immunogenic to the patient. DE 100 53 014 and WO 96/39814 describe the use of tissue engineering methods for the seeding of artificial extracellular matrices with autologous cells and the placement of such seeded matrices in a pulsatile bioreactor containing culture medium to induce the proliferation of the colonizing cells upon the extracellular matrix. The disadvantage of this approach is the fact that the tissue created by this method is artificial and less durable than autologous human tissue as a consequence of poor cellular attachment and recognition of the foreign extracellular matrix by the colonizing cells.

Document U.S. Pat. No. 5,554,184 describes the application of autologous pericardium for the construction of a heart valve replacement. The disadvantage of the disclosed method is that the pericardium is stabilized and crosslinked in a solution of glutaraldehyde which kills the cells in the tissue. A heart valve replacement constructed by this method is not viable and is subject to the same problems as the aforementioned whole porcine and bovine pericardial heart valves, with the exception of immunogenic reaction to the extracellular matrix. Documents UA 77043, UA 67333, UA 63819 and UA 63826 describe the application of autologous pericardium for the construction of a heart valve replacement, for valvuloplasty of heart valve cusps, or for the repair of heart chamber defects (UA 63826). However, the harvested autologous pericardium is also treated in glutaraldehyde which means that dead tissue is used for the implantation.

The disadvantages of the above mentioned heart valve replacements also lies in their higher stiffness inducing higher flow gradients across the valve and inferior mechanical properties (the heart valve replacements being less pliable). Heart valves constructed from dead tissue are subject to dystrophic calcification resulting in failure of function of the heart valve replacement. The lifespan of such biological replacements is 10 to 15 years after which time it is necessary to remove the heart valve replacement and substitute it with a new one. Presently used mechanical heart valve replacements require long-term anticoagulation therapy because they are thrombogenic and increase the risk of infective endocarditis which reduces the quality of life of the patient.

The objective of this invention is to create a pericardial heart valve replacement that will remain functional for the course of the patient's lifetime, a replacement that possesses the same hemodynamic, mechanical and histological properties as the native human heart valve, that will be capable of ECM production, repair, remodeling and cellular homeostasis, and which is constructed from the patient's native tissue.

SUMMARY OF THE INVENTION

The objective of the invention has been met by developing a method of constructing a pericardial heart valve replacement using modified living tissue of autologous pericardium, and by the development of a device for the in vitro conditioning and modification of living autologous pericardial tissue for the construction of a pericardial heart valve replacement.

The method of constructing a biological heart valve replacement from autologous pericardial tissue is described. In the first step the size and shape of the patient's native pathological heart valve is determined by real-time three-dimensional transesophageal echocardiography (TEE) or by computer tomography (CT angiography) or by magnetic resonance imaging (MRI). In the next step a pericardial heart valve replacement is constructed for stented or stentless implantation from a single sheet of living autologous pericardial tissue obtained from the patient containing living pericardial interstitial cells (PICs) and a living extracellular matrix (ECM). In both cases the heart valve is constructed from a single sheet of pericardium and the cusps remain connected at the commissures in a similar manner as a normal human heart valve. In the case that three pieces of pericardium are used to suture the heart valve replacement it would be necessary to suture the individual pieces at the commissures which would make the replacement more prone to damage. The shape of the heart valve replacement corresponds to the patient's native heart valve and aortic root which makes it anatomically tailored for the particular patient. By constructing the heart valve replacement from one piece of pericardium to match the shape of the patient's aortic root, the heart valve replacement acquires a form that closely resembles the patient's native heart valve. The shape is maintained by creating a specially designed stent with posts that matches the shape of the aortic root using the technique of rapid prototyping giving the pericardial heart valve replacement normal physiological shape and function. For nondegradable stents a nonabsorbable suture material is used, for absorbable (biodegradable) stents an absorbable suture material is used. Over time, biodegradable stents and absorbable suture materials are absorbed in the body of the patient after implantation leaving only living pericardial tissue of the pericardial heart valve replacement which grows into the wall of the aorta, pulmonary artery, tricuspid or mitral annulus.

For a stented pericardial heart valve replacement an anatomically tailored stent is prepared corresponding to the shape of the patient's native pathological heart valve and aortic root and the tissue of the autologous pericardium is sutured to the stent. The anatomically tailored stent models the pericardial tissue during conditioning and makes it easier for the pericardial heart valve replacement to settle in the aortic root improving its function and lifespan.

For a stentless pericardial heart valve replacement a temporary anatomically tailored holding system is prepared consisting of profiled posts. Next the autologous pericardial tissue is secured to the holding system. The anatomically tailored holding system models the shape of the pericardial tissue which gradually acquires the shape of a heart valve. After it is sutured in the aortic root, the stentless pericardial heart valve replacement maintains the shape modeled on the holding system. Because there is no stent in this heart valve replacement, a possible immune reaction to foreign material is avoided and the patient's body can more easily accept the heart valve replacement. An alternative solution is to suture the pericardial tissue to an anatomically tailored temporary stent that models the heart valve replacement during conditioning. There is only minimal suturing of commissures and the base of the heart valve replacement is secured by clamping or sealing components.

The pericardial heart valve replacement with an anatomically modeled stent undergoes in vitro dynamic conditioning and hemodynamic testing in a pulsatile bioreactor comprising a hydrodynamic circuit of an artificial heart. The hemodynamic loading of the pericardial heart valve replacement induces pericardial interstitial cell (PIC) activation and phenotypic differentiation resulting in the production and remodeling of pericardial extracellular matrix (ECM) which improves the structural properties of the pericardial heart valve replacement so that it resembles the patient's native heart valve. The dynamic conditioning induces an increase in the content of collagen and elastic fibers and glycosaminoglycans enhancing the mechanobiological properties of the tissue and the hemodynamic properties of the pericardial heart valve replacement. As a result of hemodynamic loading the histological profile of the pericardial heart valve replacement resembles the histological profile of the native human heart valve.

In an advantageous embodiment of the invention the device for conditioning and modification of the living autologous pericardial tissue creates a physiological environment for dynamic loading of the pericardial heart valve replacement with corresponding systolic and diastolic pressures of 110-140/70-80 mmHg and flow rate of the culture medium from 5 to 6 l/min. In this way the pericardial tissue is conditioned to function as a heart valve replacement. Dynamic loading conditions can be adjusted by increasing the hemodynamic pressure or pulse frequency and the behavior of the heart valve replacement can thus be monitored during periods of increased loading which normally occur in humans during physical work or exercise.

It is advantageous that the hemodynamic properties of the pericardial heart valve replacement are monitored during in vitro dynamic conditioning including the transvalvular pressure gradients and valve cusp coaptation using echocardiography or flow rate and pressure sensors in the hemodynamic circuit of the cultivation device. The pericardial heart valve replacement constructed from living pericardial tissue possesses transvalvular pressure gradients equal to that of the normal native aortic heart valve at systemic pressures (maximal up to 6 mmHg, mean 3 mmHg) with normal opening and closing of valve cusps and no regurgitation. These gradients are lower than those achieved by presently used biological or mechanical heart valve replacements.

It is an advantage of the method of this invention that the surface of the pericardial heart valve replacement is endothelialized, i.e. is covered by autologous endothelial cells. For this purpose autologous circulating endothelial progenitor cells and circulating endothelial cells will be isolated from the patient's peripheral blood by immunomagnetic separation methods or by flow cytometry. These cells will be multiplied and seeded onto the surface of the heart valve replacement in vitro using one of two approaches: (1) by infusing the endothelial progenitor cells directly into the device for dynamic conditioning with the assumption that they will spontaneously endothelialize the surface of the pericardial heart valve replacement, or (2) by seeding the endothelial progenitor cells onto the pericardial heart valve replacement in static culture (e.g. culture dish). In both cases the endothelial progenitor cells can be multiplied in vitro and pre-differentiated in the direction of endothelial cells which is influenced by the appropriate composition of the cultivation medium before seeding them onto the pericardial heart valve replacement. The correct differentiated lineage of the endothelial cells will be verified by staining for antigens of endothelial progenitor cells (EPCs)/stem cells such as CD34, CD133 and endothelial antigens KDR (VEGFR-2), CD31 and von Willebrand factor.

Another approach to endothelialization of the pericardial heart valve replacement is to isolate and use autologous endothelial cells harvested from the patient's native heart valve or endocardium by means of transcatheter endothelial biopsy from the surface of the patient's native heart valve or endocardium. From the practical point of view it is more advantageous to harvest the endothelium from the tricuspid valve or from the endocardium of the right heart chambers. These cells will be multiplied in vitro before seeding onto the autologous pericardium.

Another approach is that endothelialization of the pericardial heart valve replacement occurs entirely in vivo in the patient's body after implantation of the pericardial heart valve replacement by means of circulating endothelial progenitor cells present in the circulation of the patient.

The attachment and anchorage of endothelial cells onto the surface of the pericardial heart valve replacement is probable for the following reasons: (1) the peeling off (at least partially) of native surface pericardial mesothelial cells during heart valve replacement manipulation which uncovers the pericardial extracellular matrix, and (2) the presence of specific amino acidic sequences and other ligands for cellular adhesion receptors on the surface of the extracellular matrix which is considered an attractive substrate for endothelial cell adhesion.

In another advantageous embodiment of the invention both dynamic conditioning and endothelialization of the autologous pericardial heart valve replacement are allowed to occur naturally in vivo within the circulation of the patient after implantation of the heart valve replacement without a prior in vitro conditioning phase. Similarly to an in vitro conditioned pericardial heart valve replacement, no chemicals or crosslinking agents are used to preserve the autologous pericardial tissue and thus the tissue is maintained viable. This method is advantageous in case there is a need to implant the heart valve replacement quickly.

Through dynamic loading and endothelialization the pericardial heart valve replacement acquires a histological profile that closely resembles the histological profile of a normal human heart valve.

It is finally advantageous that during the dynamic conditioning and hemodynamic testing of the pericardial heart valve replacement in the device for conditioning and modification of living autologous pericardial tissue that at least one substance from the group is added including stem cells, progenitor endothelial cells, isolated pericardial interstitial cells, valve interstitial cells, blood products, growth factors, anticalcification agents, crosslinking agents, antibiotics, cytokines, immunomodulators and nutrients is introduced to the pericardial heart valve replacement. These substances improve the qualities of the pericardial heart valve replacement. It is possible to influence the intensity of proliferation and creation of extracellular matrix by the length of the conditioning, application of growth factors and by the endothelialization of the surface of the heart valve replacement.

Furthermore, the subject matter of the invention is that the pericardial heart valve replacement prepared according to the aforementioned method of construction is composed of living autologous pericardium containing living pericardial interstitial cells (PICs) and living extracellular matrix (ECM). Such a heart valve replacement will remain functional for the patient's lifetime. The clinical use of such a heart valve replacement will eliminate the need for long-term anticoagulation therapy and will reduce the incidence of thrombotic complications or infectious endocarditis. Injury to red bloods and hemolysis will be minimized due to better inherent properties of autologous pericardial tissue such as its physiological pliability when compared to stiffer xenogeneic biological heart valve replacements fixed with glutaraldehyde or mechanical heart valve replacements.

In an advantageous embodiment of the invention the tissue of the autologous pericardium and the sewing cuff made therefrom are arranged on the stent or on the holding system consisting of profiled posts. The shape of the pericardial heart valve replacement is thus maintained.

It is also advantageous that the stent and the sewing cuff are made from an absorbable biocompatible or biodegradable material. The shape of the pericardial heart valve replacement corresponds to the shape of the native heart valve annulus or artery root. During implantation, the heart valve replacement adheres to the heart valve annulus or artery wall after suturing. Suturing in the supraannular position is considered more advantageous. Absorbable stents temporarily support the living pericardial heart valve replacement in the anatomical position of the excised native heart valve until the sutured margins of the replacement have grown into the wall of the heart or artery root. The absorbable stent is gradually absorbed over time leaving only pericardial tissue in its place forming the heart valve.

In an advantageous embodiment of the invention the inflow part of the pericardial heart valve is sutured directly in the aortic root without the use of the stent.

The application of living autologous pericardium modified by the above method as a material for the construction of a pericardial heart valve replacement is advantageous in that it is possible to create a heart valve replacement that has a lower risk of an adverse immune response and dystrophic calcification. Living cells in the pericardial tissue are capable of cellular division and metabolic activity which allows for the regeneration of the ECM and adaptation to circulatory forces.

It is also the subject matter of the invention that a device is developed for the conditioning and modification of the living autologous pericardium of the pericardial heart valve replacement. The device consists of a pulsatile pump driving the flow of culture medium perfusing the cells in the pericardium, a reservoir for regulating the fluid capacitance and function of the pericardial heart valve replacement, a chamber for placement of the pericardial heart valve replacement where a hollow cylindrical holder for the pericardial heart valve replacement is retained, and a gas exchanger for perfusing the culture medium with air mixed with 5% $CO_2$. The reservoir for regulating the fluid capacitance, the chamber for placement of the pericardial heart valve replacement and the gas exchanger are placed in an incubator with an inner atmosphere composed of air mixed with 5% $CO_2$ and a temperature of 36 to 37° C. The individual components of the device are interconnected by tubing.

In an advantageous embodiment the chamber for placement of the pericardial heart valve replacement is made from plexiglass with plastic and metal components for visual and echocardiographic evaluation of the pericardial heart valve replacement during dynamic conditioning.

The device, in an advantageous embodiment, is equipped with sensors for pressure and/or pH and/or $pCO_2$ and/or $pO_2$ and/or temperature in front of and behind the chamber. The pericardial heart valve replacement and culture medium are continually monitored to avoid injury to the pericardial heart valve replacement during in vitro conditioning and modification.

It is advantageous for the culture medium to contain human serum, preferably the autologous serum of the patient for whom the pericardial heart valve replacement is being made. Thus the pericardial tissue is placed in its native environment to which it adapts. In another embodiment the culture medium contains other autologous blood derivatives. The pericardial heart valve replacement is thus surrounded by the patient's autologous circulatory fluids during the process of conditioning with minimal exposure to chemicals that could potentially damage the pericardial tissue and its cells.

The reservoir regulating the fluid capacitance contains a means to alter the resistance to flow of the culture medium in the device. The pressure of the fluid in the device, to which the pericardial heart valve replacement is exposed, can thus be controlled.

The tubing is equipped with infusion ports for introducing into the device at least one substance from a group including stem cells, endothelial progenitor cells, isolated pericardial interstitial cells, valve interstitial cells, blood products, growth factors, anticalcification agents, crosslinking agents, antibiotics, cytokines, immunomodulators and nutrients. These substances promote conditioning and modification of the living pericardial tissue forming the heart valve replacement.

In an advantageous embodiment of the invention the chamber is formed by a base part with an opening and by a removable part with an opening, wherein both parts have a cylindrical shape and are connected in a removable manner by means of a thread. The holder is connected with the base part which is advantageous for placement of the pericardial heart valve replacement in the chamber. The base part unscrews from the removable part, the pericardial heart valve replacement is secured to the holder to which it is sutured at three points. Then the removable part is screwed to the base part and the chamber is filled with culture medium which flows in through the opening in the base part and flows out through the opening in the removable part.

In an advantageous embodiment of the invention the hollow cylindrical holder is connected with an input part of cylindrical shape which is connected to the base part of the chamber. The culture medium flows through the hollow cylindrical holder creating a pressure simulating the blood pressure to which the pericardial heart valve replacement will be exposed in the heart of the patient after implantation.

The advantages of the pericardial heart valve replacement constructed according to the above mentioned method is the use of autologous tissue that is native to patient's body and which will not provoke an adverse immune response. This makes it easier for the patient's body to accept such a heart valve replacement after implantation. The autologous pericardial heart valve replacement is viable and therefore capable of extracellular matrix repair, remodeling and cellular homeostasis.

DESCRIPTION OF THE DRAWINGS

The invention will be described in more detail by means of drawings which show: a stentless pericardial heart valve replacement (FIG. 1), a stented pericardial heart valve replacement (longitudinal suturing method of securing the pericardium to the stent) with a sewing cuff (FIG. 2), a cross section of a stented pericardial heart valve replacement with a sewing cuff (FIG. 3), a stented pericardial heart valve replacement with a flat base and sewing cuff (circular suturing method of securing the pericardium to the stent) mounted on the holder before placement in the device for conditioning and modification (FIG. 4a), a pericardial heart valve replacement on an anatomically shaped stent with a sewing cuff (circular suturing method) mounted on the holder before placement in the device for conditioning and modification (FIG. 4b), a stented pericardial heart valve replacement with a sewing cuff (longitudinal suturing method) mounted on the holder before placement in the device for conditioning and modification (FIG. 5), a stentless pericardial heart valve replacement with a sewing cuff mounted on the holding system and secured with a straight fixation ring before placement in the device for conditioning and modification (FIG. 6a), a stentless pericardial heart valve replacement with a sewing cuff mounted on the holding system and secured with an anatomically shaped fixation ring before placement in the device for conditioning and modification (FIG. 6b), a stent made from biocompatible material with straight posts (FIG. 7a), a stent made from biocompatible material with reinforced posts at the base of the stent (FIG. 7b), a biocompatible stent with straight wire posts with loops (FIG. 8), a biocompatible stent with three wire posts with loops in the shape of the aortic root according to three-dimensional echocardiography, CT angiography or MRI (FIG. 9), a biocompatible stent with straight posts on a holder (FIG. 10), a biocompatible anatomically shaped stent (FIG. 11), a biocompatible anatomically shaped stent with a flat base and wire posts with loops (FIG. 12a), a biocompatible anatomically shaped stent with wire posts with loops (FIG. 12b), a holder for the heart valve replacement (FIG. 13), a block diagram of the device for the in vitro dynamic conditioning and modification of the pericardial heart valve replacement (FIG. 14), and the chamber for placement of the pericardial heart valve replacement during dynamic conditioning (FIG. 15).

DESCRIPTION OF THE INVENTION

Figure 1:
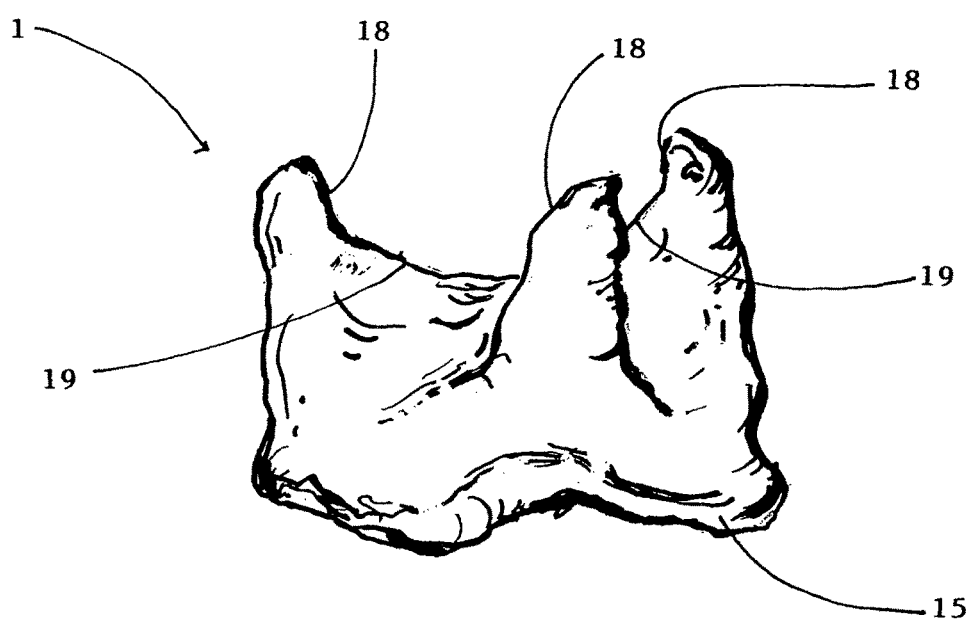
Figure 2:
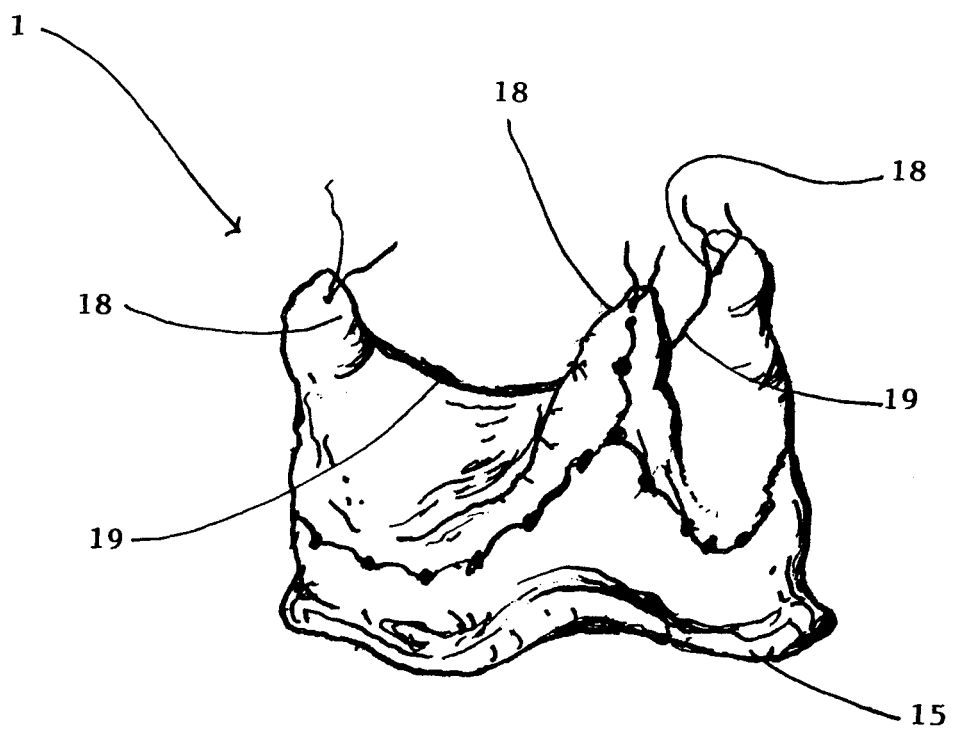
Figure 3:
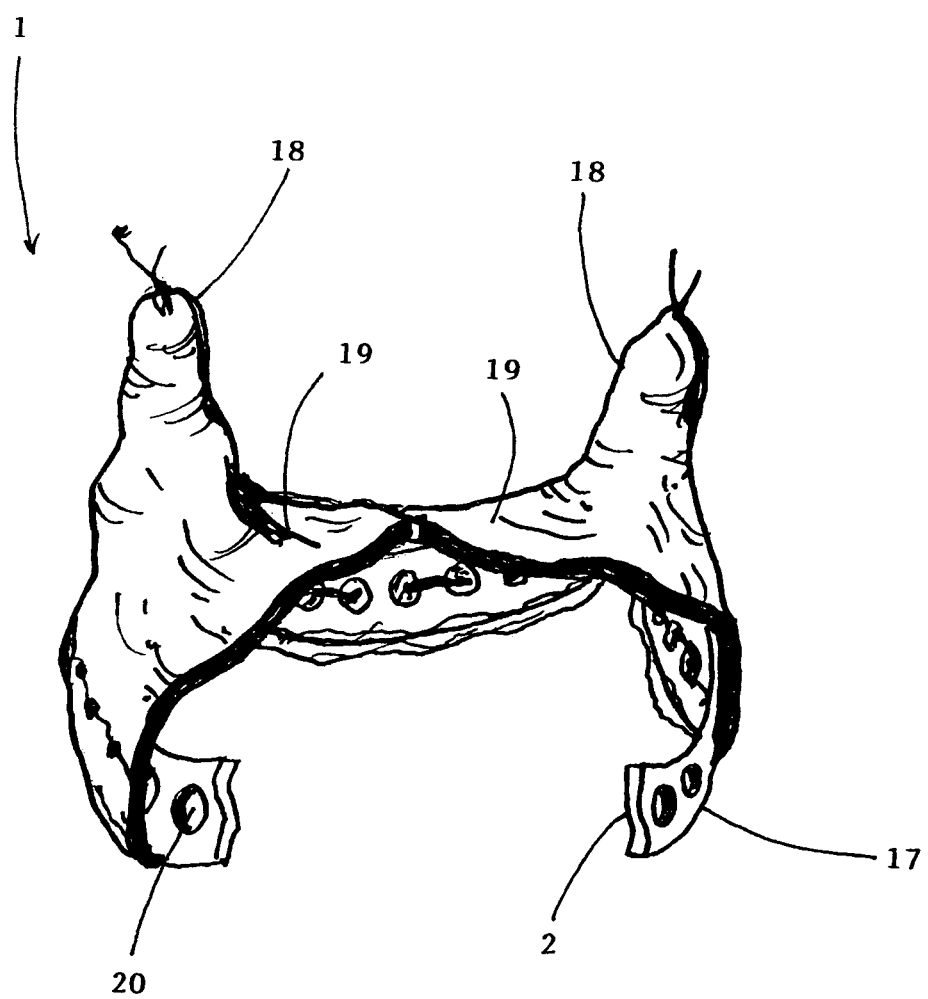
Figure 4A:
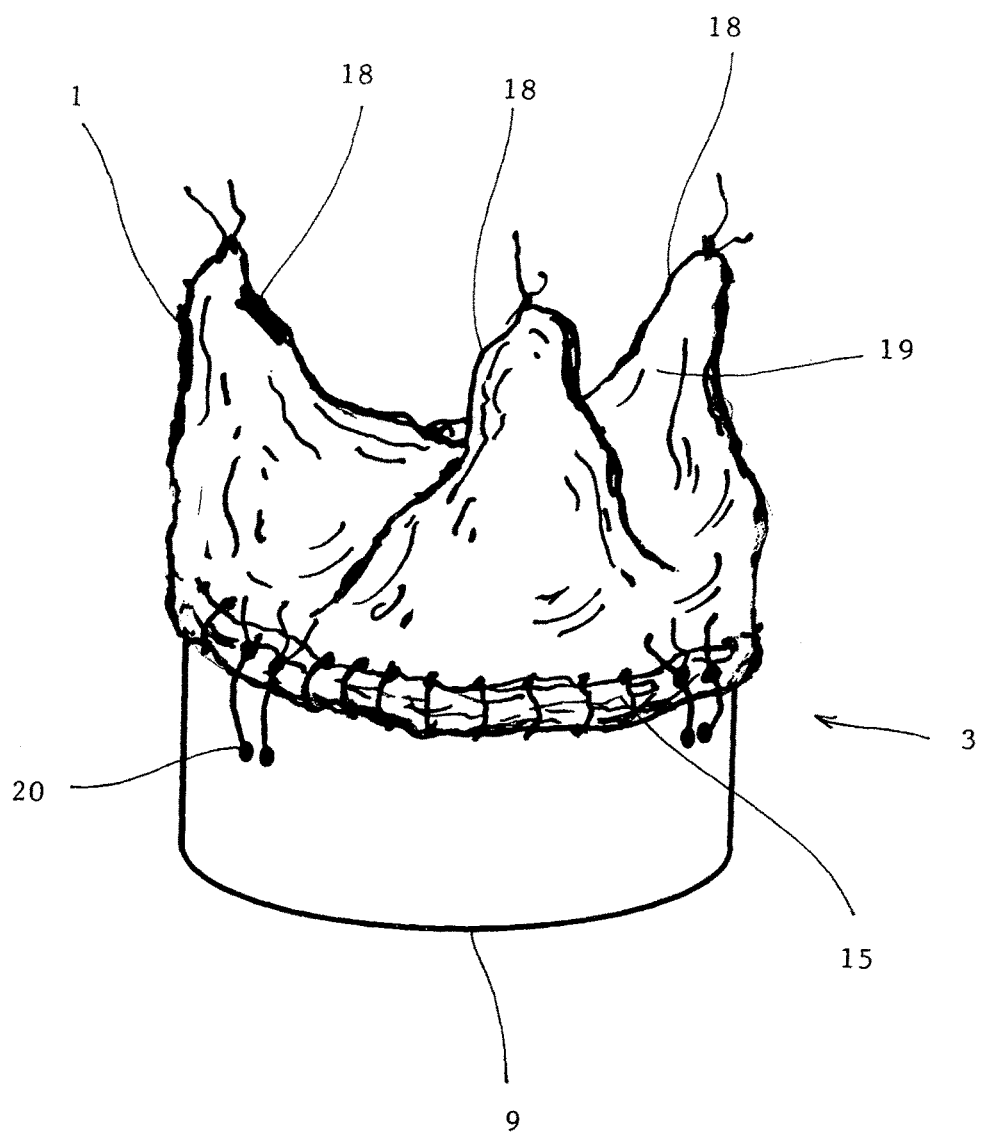
Figure 4B:
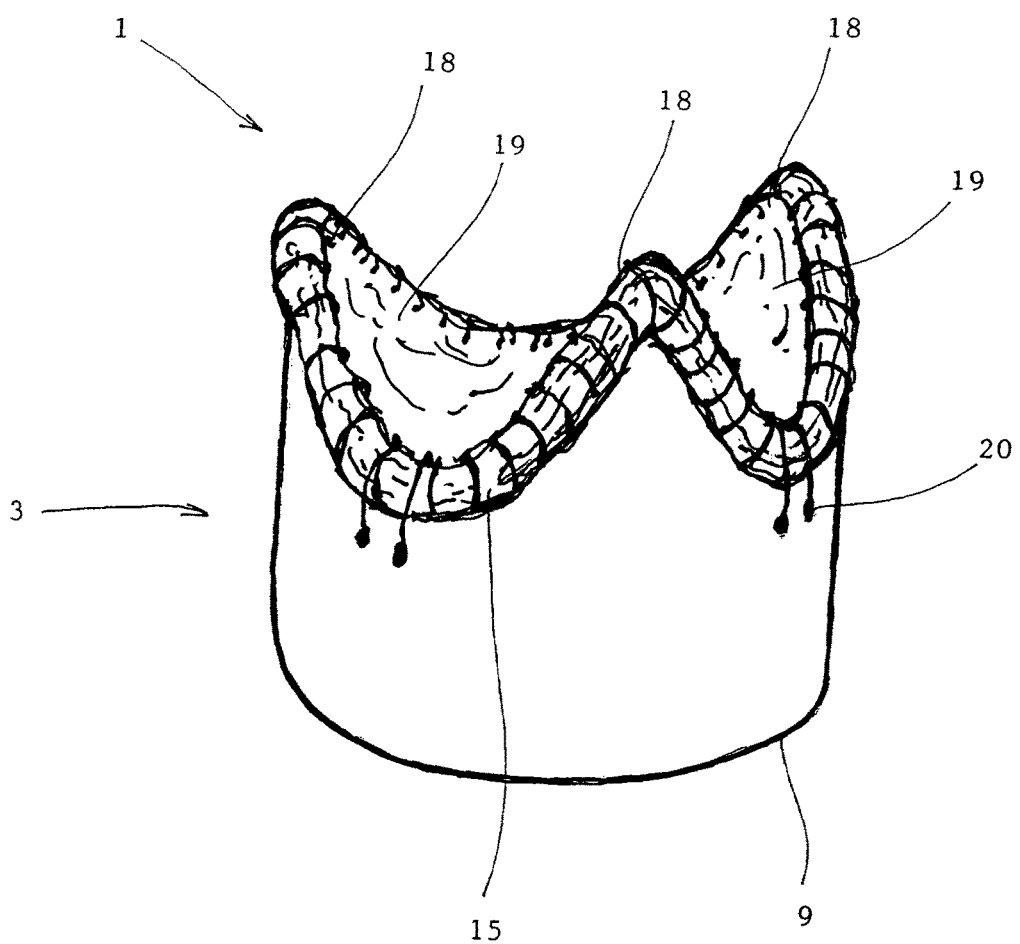
Figure 5:
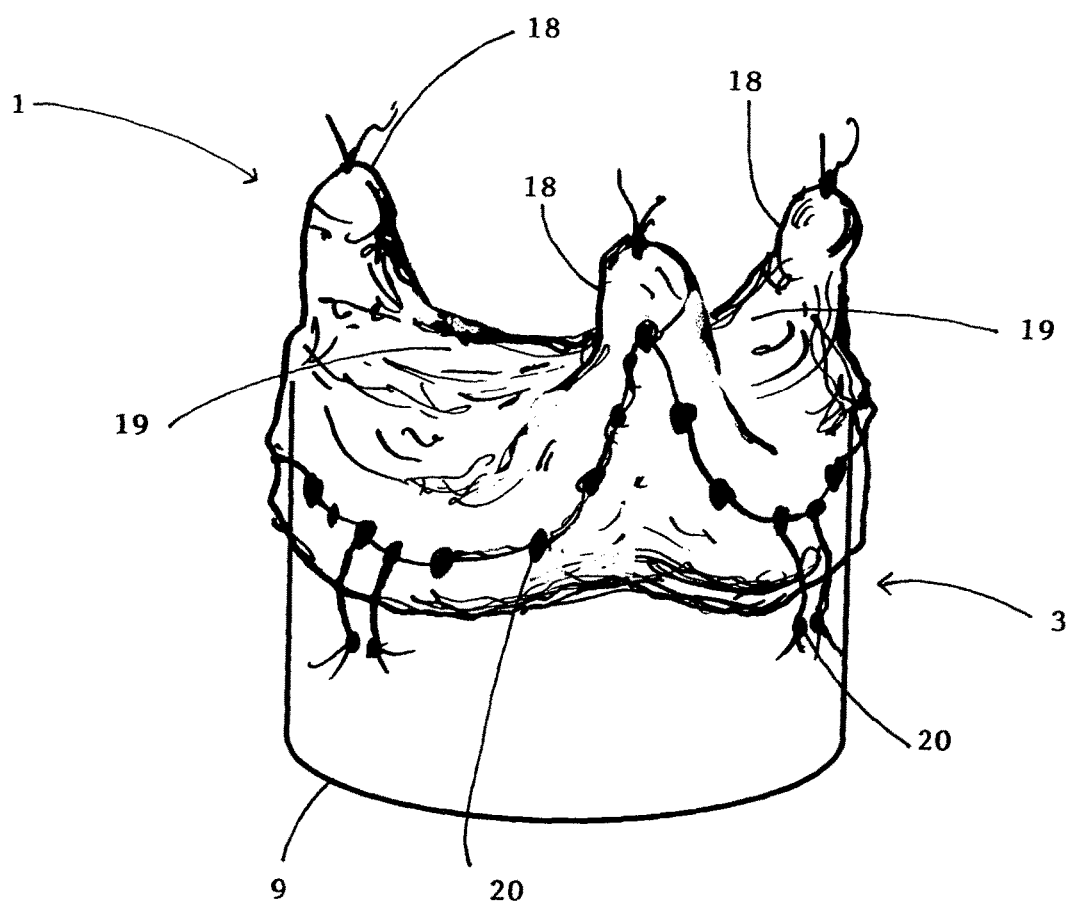
Figure 6A:
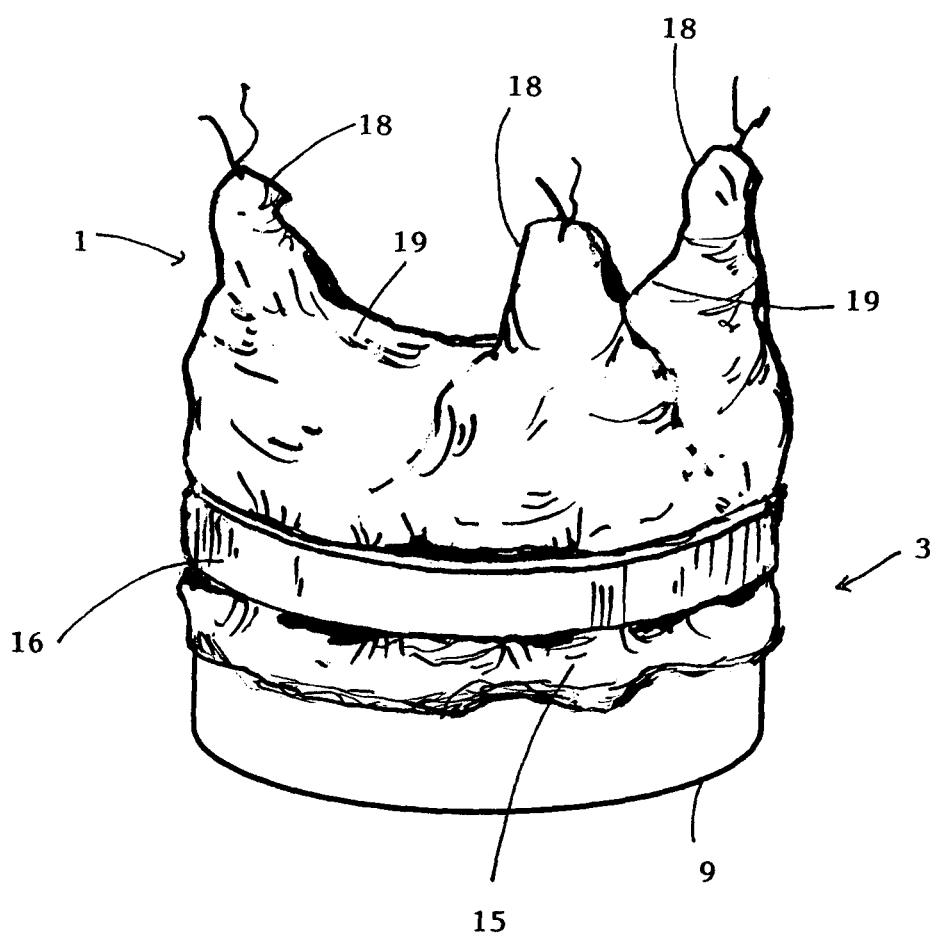
Figure 6B:
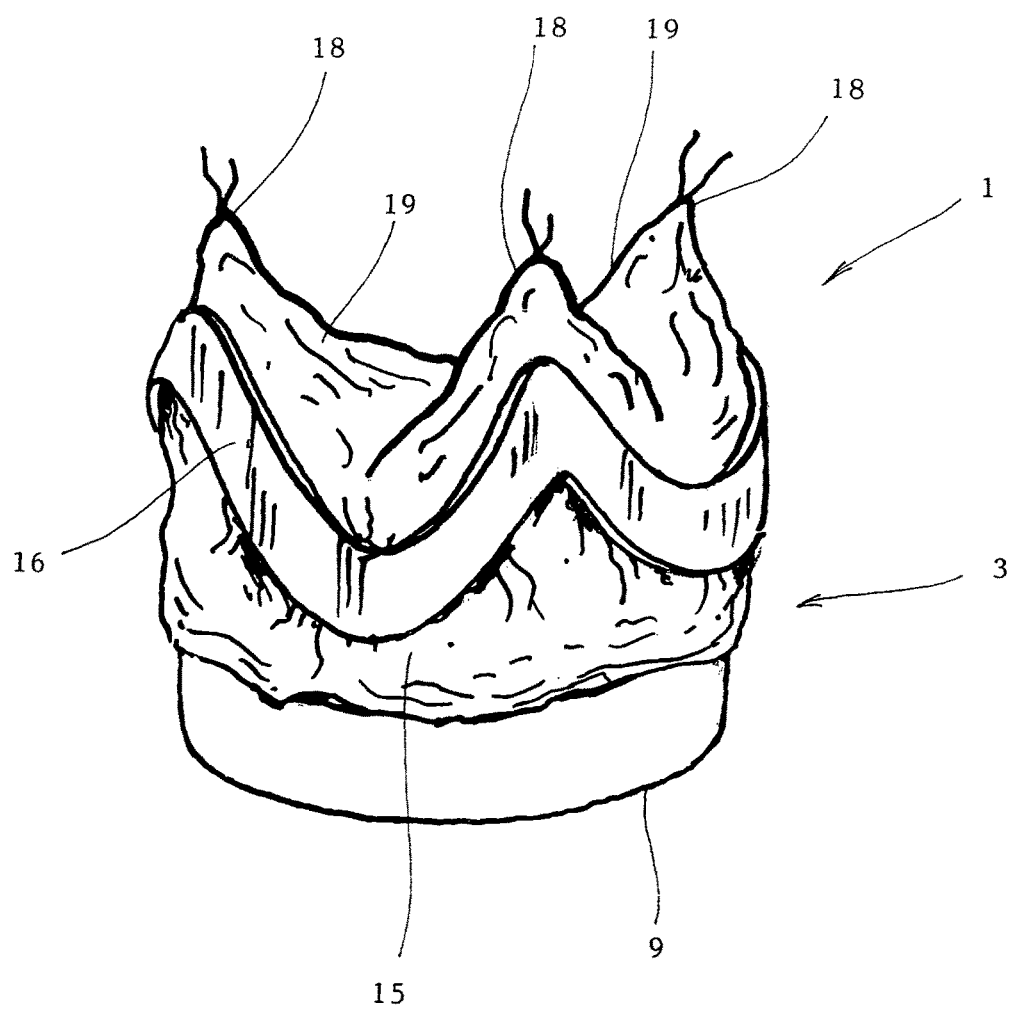
Figure 11:
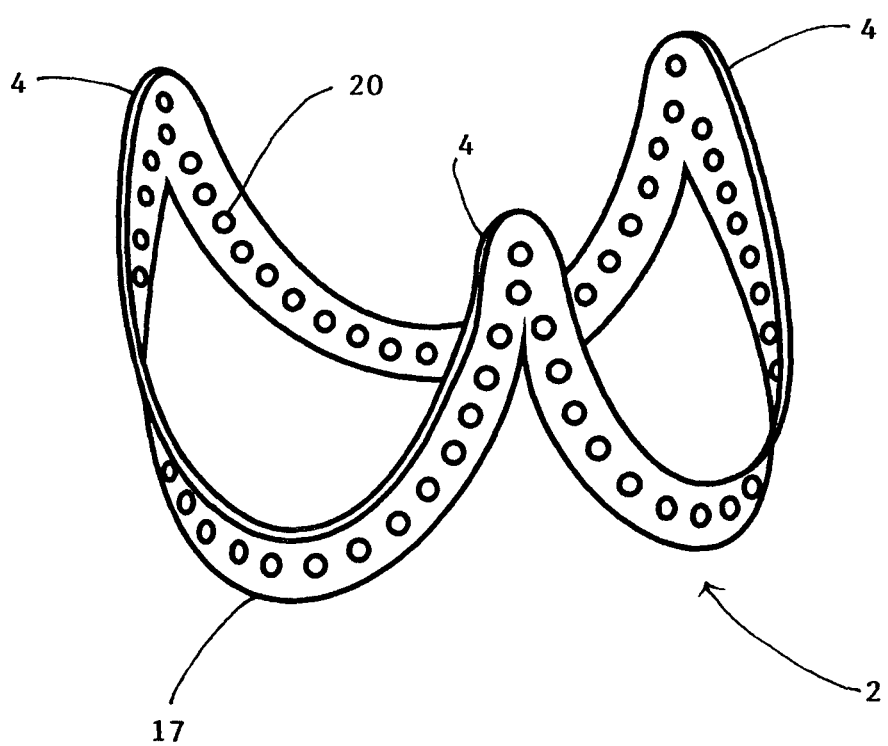
Figure 12A:
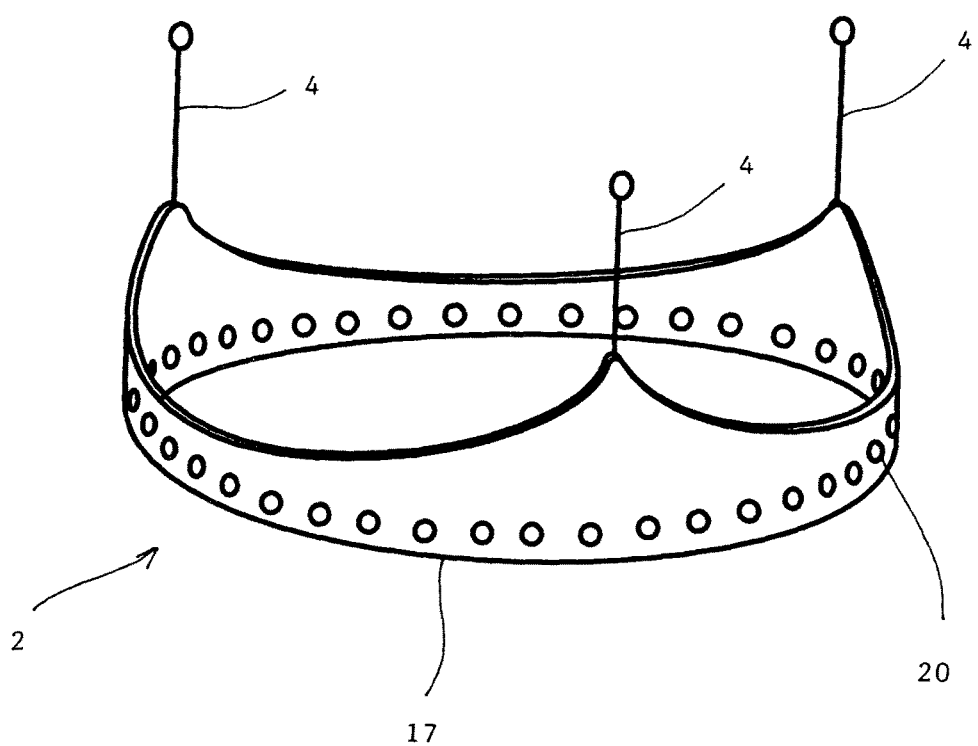
Figure 12B:
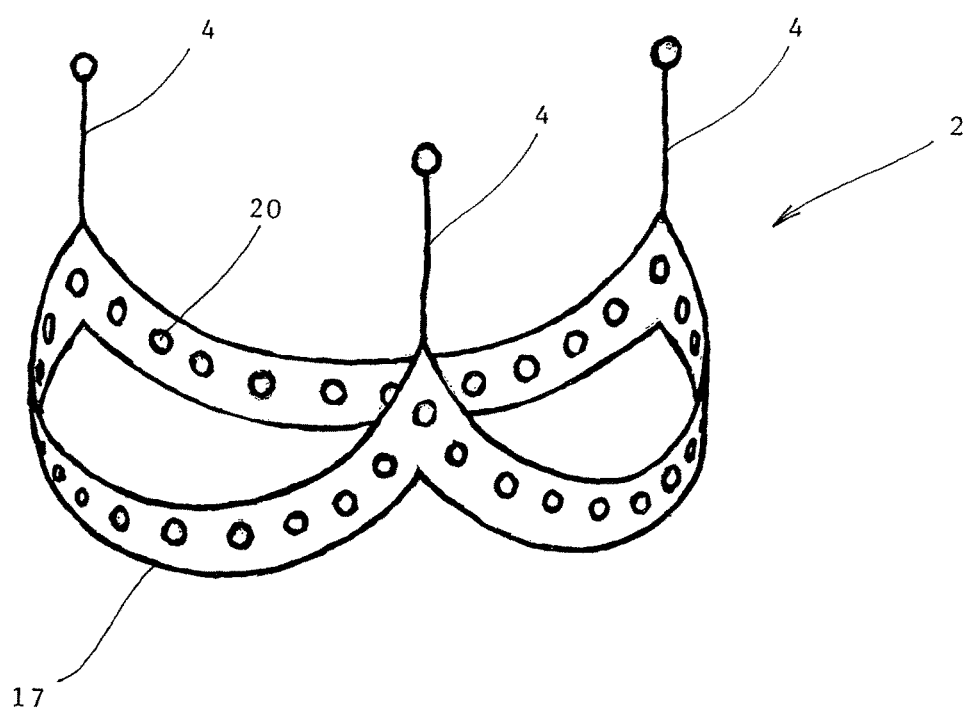
Figure 13:
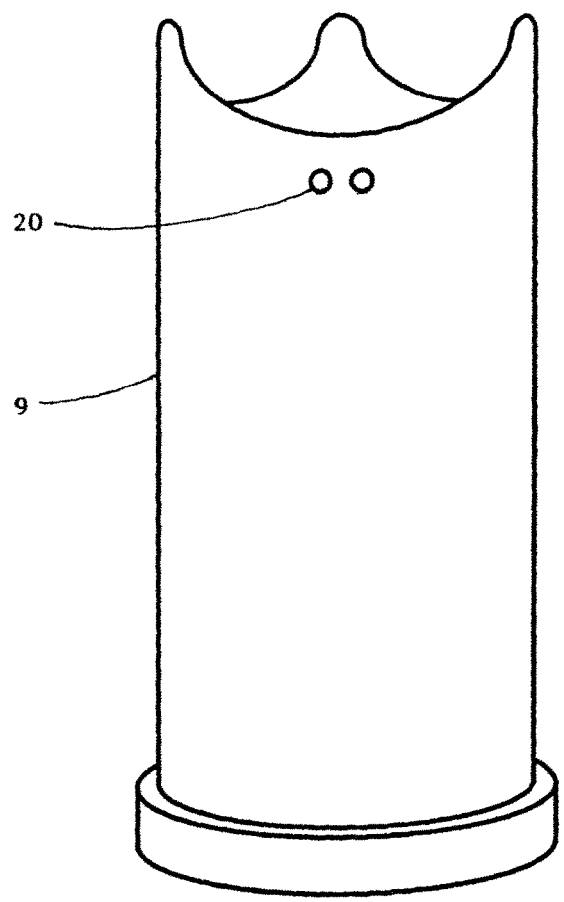

It is understood that the examples of the invention's application as described and illustrated below are presented for illustration purposes and not as a limitation of examples of the invention's application for the cases given. The experts skilled in the art will find or will be able to find, with the use of routine experimentation, either a higher or a lower number of equivalents to specific embodiments of the invention specifically described herein. Even these equivalents shall be included in the scope of the following claims.

The living pericardial heart valve replacements 1 are constructed on the basis of three-dimensional anatomic geometry of the patient's aortic root and native pathological heart valve. Before the heart valve replacement procedure, real-time three-dimensional transesophageal echocardiography (TEE), CT angiography or MRI are performed to determine the exact shape of the patient's heart valve and aortic root. Based on this information a stent 2 is produced using rapid prototyping technology, its shape and size corresponding to the shape and size of the patient's aortic root and native heart valve. This allows for the precise anatomical positioning of the pericardial heart valve replacement 1 during implantation and its eventual ingrowth into the heart or aortic root of the patient after implantation.

In the next step, the patient's autologous parietal pericardium is harvested by pericardiectomy. The harvesting is carried out using minimally invasive methods and flexible instruments applying technology such as pericardioscopy, cutting instruments (laser, thermal or harmonic scalpel) and flexible graspers. The harvesting procedure is performed under sterile operative conditions in the surgical theater under local anesthesia or mild general anesthesia (e.g. using Propofol). The procedure involves the subxyphoid or apical cannulation of the pericardial cavity under echocardiographic control or direct endoscopic vision and the introduction of a guidewire followed by a flexible endoscopic instrument with an optical system and cutting device. This 15-20 French flexible instrument (e.g. pericardioscope or catheter) has an optical channel for visualization of the internal part of the parietal pericardium and a laser or electrocautery cutting blade on the flexible ending of the instrument or introduced through the working channel of the instrument. The whole system is flexible and allows for free movement of the instrument during visualization and cutting of the pericardium inside the pericardial cavity. The harvesting of the patient's autologous pericardium is carried out under optical control to ensure patient safety during the procedure. This allows for hemostasis of any bleeding sites. The instrument is manually controlled or it is possible to use a computer guiding system with robotic control. Such a flexible instrument is able to perform both pericardioscopy and pericardiectomy. Once a sheet of autologous pericardium of desired size is harvested from the patient, a drain is left in the pericardial cavity until the second day after harvesting to drain any serous fluid and monitor for any possible bleeding. Three-dimensional echocardiography, CT and MRI of the patient's pericardial cavity assess the best location for pericardial harvesting prior to the procedure and can help determine patient eligibility to undergo pericardial harvesting. Such imaging can detect the presence of any pericardial adhesions, calcifications, pericardial fluid and the proximity of the pericardium to the heart.

Most patients suffering from heart valve disease can be stabilized for a period of time using medications. It is therefore possible to perform heart valve replacement sizing and autologous pericardial harvesting in advance of heart valve replacement implantation in most instances. A sheet of pericardium of 7.5-11 by 2.5-3 cm is sufficient to construct a heart valve in various sizes. The size of the harvested pericardium depends on the size of the patient's pathological heart valve to be replaced. The harvested pericardium is immediately transported to a sterile manufacturing site for pericardial heart valve replacement construction and dynamic conditioning in sealed sterile culture medium (Dulbecco's Modified Eagle's Medium [DMEM], 10% fetal bovine serum [FBS], 2% antibiotic/antimycotic solution) at body temperature to maintain PIC viability. A small section of pericardium can be assessed by confocal microscopy at this time to visualize the quality and concentration of PICs and ECM. Only pericardium of adequate quality is selected for heart valve replacement construction and implantation.

The living human pericardial heart valve replacement 1 can be constructed in three models:
1. Stented pericardial heart valve replacement using a stent 2 manufactured from an absorbable biodegradable material for open surgical implantation
2. Stentless pericardial heart valve replacement for open surgical implantation
3. Stented pericardial heart valve replacement using a stent 2 manufactured from an absorbable biodegradable material for transcatheter implantation.

It is also possible to use nonabsorbable biocompatible stents in the construction of stented pericardial heart valve replacements for both surgical and transcatheter implantation.

A stented living human pericardial heart valve replacement 1 using a stent 2 made from an absorbable biodegradable material is designed for supraannular implantation to maximize the effective valve orifice area of the pericardial heart valve replacement 1 and to reduce the resistance to blood flow. It is designed for open surgical implantation or transcatheter delivery, and it is necessary to remove the pathological native heart valve at the time of implantation. Absorbable biodegradable stents 2 temporarily fixate the living pericardial heart valve replacement 1 in the anatomical position of the native heart valve until heart valve replacement ingrowth occurs into the wall of the heart or aortic/pulmonary root. Over time these stents 2 are gradually absorbed leaving pericardial tissue forming the heart valve replacement 1 in its position. Absorbable stents 2 are manufactured from polylactic acid, polyglycolic acid, $\epsilon$-caprolactam, polyhydroxyalkanoate or other biocompatible absorbable biopolymers.

The stent 2 for open surgical implantation consists of a base 17 at the inflow to match the shape of the aortic annulus of the patient. From the base 17 three posts 4 extend which form and suspend the commissures 18 of the pericardial heart valve replacement 1. Stent 2 shape, circumference, post 4 height and post 4 spacing depend on the size of the desired heart valve replacement 1 for each individual patient as determined by heart valve and aortic root imaging as described above (using echocardiography, CT or MRI). The thickness of the stent 2 depends on the material from which it is manufactured. The biodegradable and biopolymer stents 2 may be thicker than wire frame (nitinol, titanium, Elgiloy) stents 2 to maintain their strength and functionality.

The stents 2 for construction of a living human pericardial heart valve replacement 1 are designed in two embodiments. In the first embodiment the sewing cuff 15 is attached to the stent 2 and is a part of the pericardium from which the heart valve replacement 1 is sutured.

In the second embodiment the stent 2 and the sewing cuff 15 are two separate components assembled together with sutures or clips after the pericardium has been sutured to the stent 2. This separate arrangement simplifies suturing the pericardium to the stent 2 and allows for the use of larger sewing cuffs 15 when irregularities in the aortic annulus need be sealed. Stents 2 and sewing cuffs 15 are preferably coated or impregnated with various agents to enhance their resistance to thrombosis, anticalcification or retard pannus overgrowth, such as alpha oleic acid or Carbofilm.

The stentless living pericardial heart valve replacement 1 for open surgical implantation involves suturing the human pericardial heart valve replacement 1 directly in place of the native heart valve without the use of a stent 2. The size and shape of the heart valve replacement 1 annulus and height of commissural attachments is determined by three-dimensional imaging (echocardiography, CT or MRI) of the patient's native heart valve and aortic or pulmonary root before construction of the pericardial heart valve replacement 1. The commissures 18 of such a valve replacement 1 can be formed from tissue of modified pericardium backed by woven polyester material or other biocompatible or absorbable material. In the case of aortic heart valve replacement, these tabs are sutured into the aortic wall to affix the commissural attachment sites near the sino-tubular junction. The inflow part of such pericardial heart valve replacement 1 is sutured directly onto the heart valve annulus or aortic or pulmonary artery wall. It can be fitted with a sewing cuff 15 made from autologous pericardial tissue that will promote the ingrowth of the pericardial heart valve replacement 1 with the heart valve annulus. It is also possible to use a sewing cuff 15 made from woven polyester fabric or other biocompatible material that is commonly used at present time.

An alternative method of suturing a stentless living human pericardial heart valve replacement 1 involves the cutting of a tricuspid heart valve replacement from a sheet of modified pericardium using a cutting instrument. A predefined shape is cut from the modified pericardium as determined by three-dimensional imaging of the patient's native heart valve. The valve is sutured above the heart valve annulus in the shape of the patient's heart valve.

Figure 14:
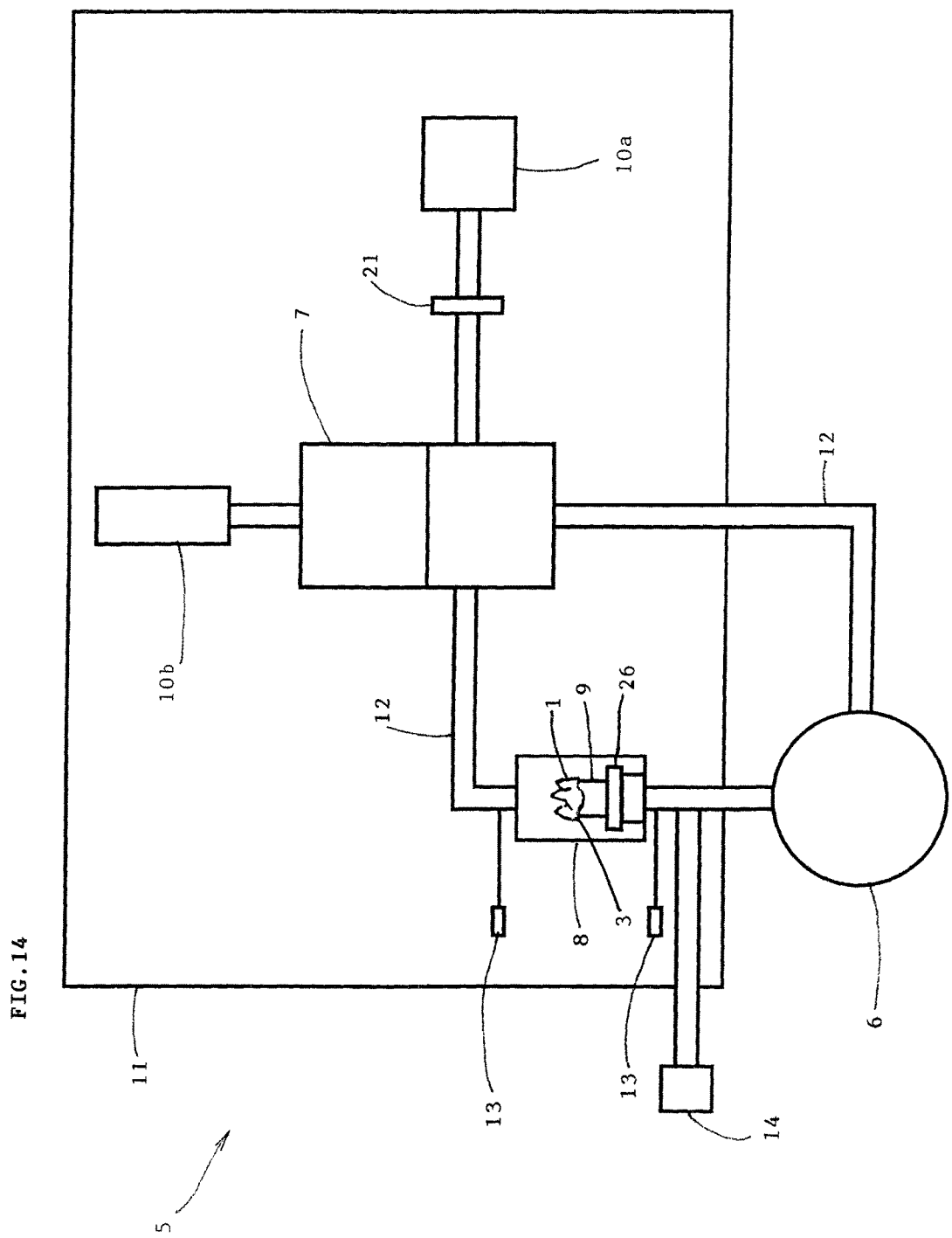

The stentless living human pericardial heart valve replacement 1 is secured to a temporary anatomically shaped stent 2 which is used to suspend and form the stentless pericardial heart valve replacement 1 in the shape of the patient's native heart valve during dynamic loading in the device 5 for conditioning and modification (see FIG. 14) of the living autologous pericardial tissue. After 7 to 21 days of dynamic conditioning the stentless pericardial heart valve replacement 1 is removed from the temporary stent 2 and implanted in the heart of the patient either by open surgical implantation or by transcatheter delivery.

The living pericardial heart valve replacement 1 for transcatheter implantation is attached to a collapsible absorbable biodegradable stent 2. It is deployed via the femoral artery or vein using transcatheter delivery. Such a pericardial heart valve replacement 1 can be self-expanding or be balloon expandable. The stent 2 can be fitted with external barbs to facilitate fixation of the heart valve replacement 1 in the native heart valve position. It is implanted by the endovascular and endocardial approach using endovascular technologies.

After pericardial harvesting, the autologous pericardium is immediately placed in cell culture medium to maintain cell viability. Before heart valve replacement 1 construction, the pericardium is first stripped of any surface adipose (fatty) tissue and is trimmed to the desired size forming a rectangular sheet.

For stent suturing, the sheet of autologous pericardium is then wrapped around the stent 2. The pericardium is sutured to the stent 2 to create a tight seal at the base 17 of the stent 2. Three posts 4 on the stent 2 suspend the pericardium creating the heart valve commissures 18. Complete coaptation of the cusps 19 of the pericardial heart valve replacement 1 is maintained during suturing of the pericardium to the stent base 17 and posts 4. One method of suturing involves folding the pericardium over the apex of each post 4 which is then secured by three sutures forming the valve commissures 18. Another method involves suturing the pericardium to the stent 2 in a continuous fashion along the posts 4 and base 17 forming the heart valve commissures 18 and cusps 19. In both instances it is possible to form the sewing cuff 15 from the autologous pericardium without using an artificial cuff made from polyester or similar materials that are presently used for this purpose. In such a case, the pericardial heart valve replacement 1 is implanted by directly suturing the autologous pericardial cuff to the patient's heart valve annulus.

During preparation and suturing of the living pericardial heart valve replacement 1 it is necessary to irrigate the autologous tissue of the pericardium with culture medium at intervals of one minute to maintain the viability of the tissue. The construction of the heart valve replacement 1 should not take longer than 15-30 minutes.

After suturing the autologous pericardium to the stent 2, the living pericardial heart valve replacement 1 is secured to the holder 9 for the pericardial heart valve replacement 1 which is a part of the holding system 3 and is then sealed in the chamber 8 which is a part of the device 5 (see FIG. 14) for the in vitro conditioning and modification of the living pericardial heart valve replacement 1.

The device 5 for conditioning and modification of the living autologous tissue of pericardium consists of a pulsatile pump 6 driving the cell culture medium, a reservoir 7 for regulating the fluid capacitance and function of the pericardial heart valve replacement 1, a chamber 8 for placement of the pericardial heart valve replacement 1 in which the holder 9 for the pericardial heart valve replacement 1 is retained, a gas exchanger 10*a, b* connected to the reservoir 7 for perfusing the culture medium with air mixed with 5% $CO_2$. The individual components of the device 5 are connected by tubing 12. The reservoir 7 for regulating the fluid capacitance, the chamber 8 for placement of the pericardial heart valve replacement 1 and the gas exchanger 10*a, b* are placed in an incubator 11 with an inner atmosphere of air mixed with a 5% $CO_2$ at body temperature between 36 to 37° C. The device 5 is preferably installed with sensors 13 before and after the chamber 8 to monitor the pressure and the state of the culture medium during dynamic conditioning such as the pH, $pCO_2$, $pO_2$ and temperature.

The culture medium contains DMEM, 10% FBS, 2% antibiotic/antimycotic solution and preferably autologous serum of the patient for whom the pericardial heart valve replacement 1 is being prepared. The culture medium thus preferably contains autologous serum or other blood derivatives obtained from the patient.

The reservoir 7 for regulating the fluid capacitance is provided with a means to control the resistance to the flow of the culture medium in the device 5. In this way it is possible to regulate the hydrostatic pressure corresponding to the systolic and diastolic pressure of the human circulation (120-140/60-80 mmHg). The hydrostatic pressure serves to open and close the valve cusps 19 of the pericardial heart valve replacement 1. Adjusting the level of hydrostatic pressure is based on information obtained from pressure sensors 13 positioned before and after the chamber 8 for placement of the pericardial heart valve replacement. Its value can also be regulated by the position of the reservoir 7 in relation to the chamber 8 or by changing the diameter of the tubing 12 leading from the chamber 8. The device 5 for conditioning and modification of the pericardial heart valve replacement 1 is filled with culture medium at the beginning of dynamic conditioning. The culture medium flows through the various interconnected components of the device 5 during dynamic conditioning.

The reservoir 7 for regulating the fluid capacitance is provided with infusion ports 14 for changing the culture medium and for infusing various types of cells or nutrients into the culture medium during dynamic conditioning. In this way at least one or a combination of the following substances or cells can be infused into the culture medium during dynamic conditioning: stem cells, endothelial progenitor cells, isolated PICs, valve interstitial cells, blood products, growth factors, anticalcification agents, crosslinking agents, antibiotics, cytokines, immunomodulators and nutrients.

The device 5 for conditioning and modification of the autologous pericardial heart valve replacement 1 embodies an automatic computer monitoring system for measuring desired data during dynamic conditioning. Sensors 13 are positioned before and after the chamber 8 for monitoring the hydrostatic pressure, pH, $pCO_2$, $pO_2$ and temperature of the culture medium.

The chamber 8 consists of a base part 22 with an opening 23 and a removable part 24 with an opening 25. Both parts 22 and 24 are cylindrical in shape and are connected by means of a thread 28. The removable part 24 is easily unscrewed from the base part 22 for placement of the pericardial heart valve replacement 1 onto the holder 9. The pericardial heart valve replacement 1 is secured to the holder 9 by three sutures passing through the sewing apertures 20 of the holder 9. It is also possible to use a fixation ring 16 which is pulled over the pericardial heart valve replacement 1 after being mounted on the holder 9.

In case of stentless pericardial heart valve replacements 1 a temporary stent 2 is mounted on the holder 9 to place the pericardial heart valve replacement 1 thereon. The sutured pericardial tissue is then shaped in the shape of a heart valve.

The hollow cylindrical holder 9 is connected with the cylindrical input part 26 which is connected with the base part 22 by means of a thread 27. The chamber 8 is filled with culture medium flowing into the chamber 8 through the opening 23 and then flows through the input part 26 and the holder 9. It exposes the pericardial heart valve replacement 1 to the same systolic and diastolic pressure to which it will be exposed in the heart. The hydrostatic pressure and pulse frequency of the culture medium can be regulated by increasing or decreasing the diameter of the tubing 12, by setting the pump 6 function and by adjusting the fluid capacitance of the reservoir 7.

The pericardial heart valve replacement 1 composed of autologous pericardium is conditioned in the device 5 for the in vitro conditioning and modification of the heart valve replacement. The optimal length of conditioning is between one to three weeks after which time the extracellular matrix of the living autologous pericardium is sufficiently strengthened and remodeled. During this period, the number of PICs increases by two to four fold. The pericardial tissue of the heart valve replacement 1 thus acquires properties of normal heart valve tissue, including anatomical, hemodynamic, histological and mechanical. The living autologous pericardial heart valve replacement 1 with an endothelialized surface will have a lower incidence of thrombotic complications, dystrophic changes, calcification, and functional failure resulting from an adverse immune response in comparison to xenogeneic biological heart valve replacements where such complications occur after several years following implantation. The living PICs of the pericardial heart valve replacement 1 are capable of cellular division, metabolic activity and production of ECM permitting the regeneration of the heart valve replacement tissue and its adaptation to circulatory forces. The autologous pericardial heart valve replacement 1 is not immunogenic to its recipient and contains surface ligands that will promote surface endothelialization with endothelial cells or endothelial progenitor cells in vitro or in vivo.

INDUSTRIAL APPLICABILITY

According to this invention, the described method of constructing a pericardial heart valve replacement, the pericardial heart valve replacement itself and the device for the conditioning and modification of tissue of autologous pericardium can be used for the manufacturing and implantation of heart valve replacements in patients of all age categories due to a lower incidence of heart valve replacement failure, avoidance of chronic anticoagulation therapy, and lower risk of thrombotic, bleeding and infectious complications that would necessitate reoperation or therapeutic intervention.

REFERENCES 1 pericardial heart valve replacement
2 stent
3 holding system
4 post
5 device for in vitro conditioning and modification of the pericardial heart valve replacement
6 pulsatile pump
7 reservoir for regulating the fluid capacitance
8 chamber for placement of the pericardial heart valve replacement
9 holder for the pericardial heart valve replacement
10a gas exchanger—for input of air mixed with 5% $CO_2$ into the culture medium during dynamic conditioning
10b gas exchanger—outlet for metabolic gases from the device during dynamic conditioning
11 incubator
12 tubing
13 sensor
14 infusion port
15 sewing cuff
16 fixation ring
17 stent base
18 commissure of the pericardial heart valve replacement
19 cusp of the pericardial heart valve replacement
20 sewing apertures
21 filter
22 base part of the chamber
23 opening in the base part of the chamber
24 removable part of the chamber
25 opening in the removable part of the chamber
26 input part of the holder
27 thread connecting the input part to the base part of the chamber
28 thread connecting the base part to the removable part of the chamber

LIST OF ABBREVIATIONS

CT computer tomography
DMEM Dulbecco's Modified Eagle's Medium
ECM extracellular matrix
FBS fetal bovine serum
MRI magnetic resonance imaging
PICs pericardial interstitial cells
TEE transesophageal echocardiography

The invention claimed is:

1. A method of constructing a pericardial heart valve replacement made from tissue of living autologous pericardium comprising:
    determining the size and shape of the patient's native pathological heart valve by real-time three-dimensional transesophageal echocardiography (TEE) or computer tomography (CT angiography) or by magnetic resonance imaging (MRI);
    constructing a living pericardial heart valve replacement for stented or stentless implantation from a single sheet of dynamically conditioned living autologous pericardium containing living pericardial interstitial cells (PICs) and a living extracellular matrix (ECM);
    tailoring the size and shape of the heart valve replacement so as to match the size and shape of the patient's native heart valve and aortic root; and
    dynamic conditioning and hemodynamic testing for conditioning and modification of the living autologous pericardium a device for a period of approximately 7 to 21 days in a device, the device comprising a hydrodynamic circuit of an artificial heart whereby hemodynamic loading of the living pericardial heart valve replacement induces pericardial interstitial cell (PIC) activation and phenotypic differentiation resulting in the production and remodeling of pericardial extracellular matrix (ECM) with an increase in the content of collagen and elastic fibers and glycosaminoglycans, thereby improving the mechanobiological and hemodynamic properties of the living pericardial heart valve replacement.

2. The method according to claim 1, further comprising for a stentless living pericardial heart valve replacement:
    preparing a temporary anatomically tailored holding system to model the shape of the living pericardial heart valve replacement comprising a holder with profiled posts or a temporary stent; and
    securing the living autologous pericardial tissue to the holding system by sutures through apertures in the holder, whereby the living pericardial heart valve replacement is removed from the holding system after completion of conditioning.

3. The method according to claim 1, wherein the device for conditioning and modification of the living autologous pericardial heart valve replacement creates a physiological environment for the dynamic loading of the living autologous pericardium at systolic and diastolic pressures of 110-140/70-80 mmHg and flow rate of culture medium around 5-6 l/min.

4. The method according to claim 1, wherein during the dynamic conditioning, the hemodynamic properties of the living pericardial heart valve replacement are measured including the transvalvular pressure gradients and the coaptation of valve cusps of the living pericardial heart valve replacement using echocardiography or flow rate and pressure sensors.

5. The method according to claim 1, wherein autologous circulating endothelial progenitor cells and circulating endothelial cells are used for endothelialization of the surface of the living pericardial heart valve replacement, these cells being isolated from the patient's blood by immunomagnetic separation methods or by flow cytometry and multiplied in vitro, or autologous endothelial cells are used for endothelialization of the surface of the living pericardial heart valve replacement, these cells being harvested from the patient's native heart valve using catheter endothelial biopsy of the surface of the native heart valve or endocardium and multiplied in vitro.

6. The method according to claim 1, wherein endothelialization is carried out in vitro in a static culture or in the device for conditioning and modification of the living autologous pericardium.

7. The method according to claim 1, wherein during dynamic conditioning and/or hemodynamic testing of the living pericardial heart valve replacement at least one of stem cells, endothelial progenitor cells, isolated pericardial interstitial cells, valve interstitial cells, blood products, growth factors, anticalciftcation agents, crosslinking agents, antibiotics, cytokines, immunomodulators, or nutrients is added to a culture medium.

* * * * *